U005501670A

United States Patent [19]
Sak

[11] Patent Number: 5,501,670
[45] Date of Patent: Mar. 26, 1996

[54] SYRINGE SYSTEM PROVIDING RETRACTION OF NEEDLE CANNULA INTO DISPOSABLE CARTRIDGE

[76] Inventor: Robert F. Sak, 9674 Colorado Ct., Boca Raton, Fla. 33498

[21] Appl. No.: 414,498

[22] Filed: Mar. 31, 1995

[51] Int. Cl.⁶ ..................................................... A61M 5/00
[52] U.S. Cl. ........................ 604/110; 604/195; 604/232
[58] Field of Search ...................................... 604/110, 195, 604/198, 232, 263, 218

[56] References Cited

U.S. PATENT DOCUMENTS

| | | |
|---|---|---|
| 2,002,024 | 5/1935 | Wood . |
| 4,026,287 | 5/1977 | Haller . |
| 4,245,654 | 1/1981 | Raitto . |
| 4,466,426 | 8/1984 | Blackman . |
| 4,804,370 | 2/1989 | Haber et al. . |
| 4,808,169 | 2/1989 | Haber et al. . |
| 4,813,936 | 3/1989 | Schroeder . |
| 4,838,870 | 6/1989 | Haber et al. . |
| 4,931,040 | 6/1990 | Haber et al. ........................ 604/232 X |
| 4,950,241 | 8/1990 | Ranford . |
| 4,995,870 | 2/1991 | Baskas . |
| 5,047,016 | 9/1991 | Dolgin et al. . |
| 5,088,988 | 2/1992 | Talonn et al. ........................ 604/232 X |
| 5,188,597 | 2/1993 | Sweeney et al. . |
| 5,201,719 | 4/1993 | Collins et al. ........................ 604/195 |
| 5,221,262 | 6/1993 | Kite . |
| 5,290,233 | 3/1994 | Campbell . |
| 5,382,235 | 1/1995 | Sak . |

Primary Examiner—John D. Yasko
Attorney, Agent, or Firm—Banner & Allegretti, Ltd.

[57] ABSTRACT

A cartridge based syringe system utilizes a cartridge piston having an interlocking needle receiving cup and retraction cage structure graspable by a conventional plunger hook, and a break-away needle assembly, in order to provide simple and reliable retraction of a needle cannula into a disposable medicant cartridge. Needle retraction is accomplished by simply reversing the movement of the plunger at the end of an injection stroke. A conventional type of dental syringe can be readily converted into a safety syringe providing the aforementioned needle retraction simply by replacing the disposable parts, i.e., the needle assembly and the medicant cartridge.

17 Claims, 5 Drawing Sheets

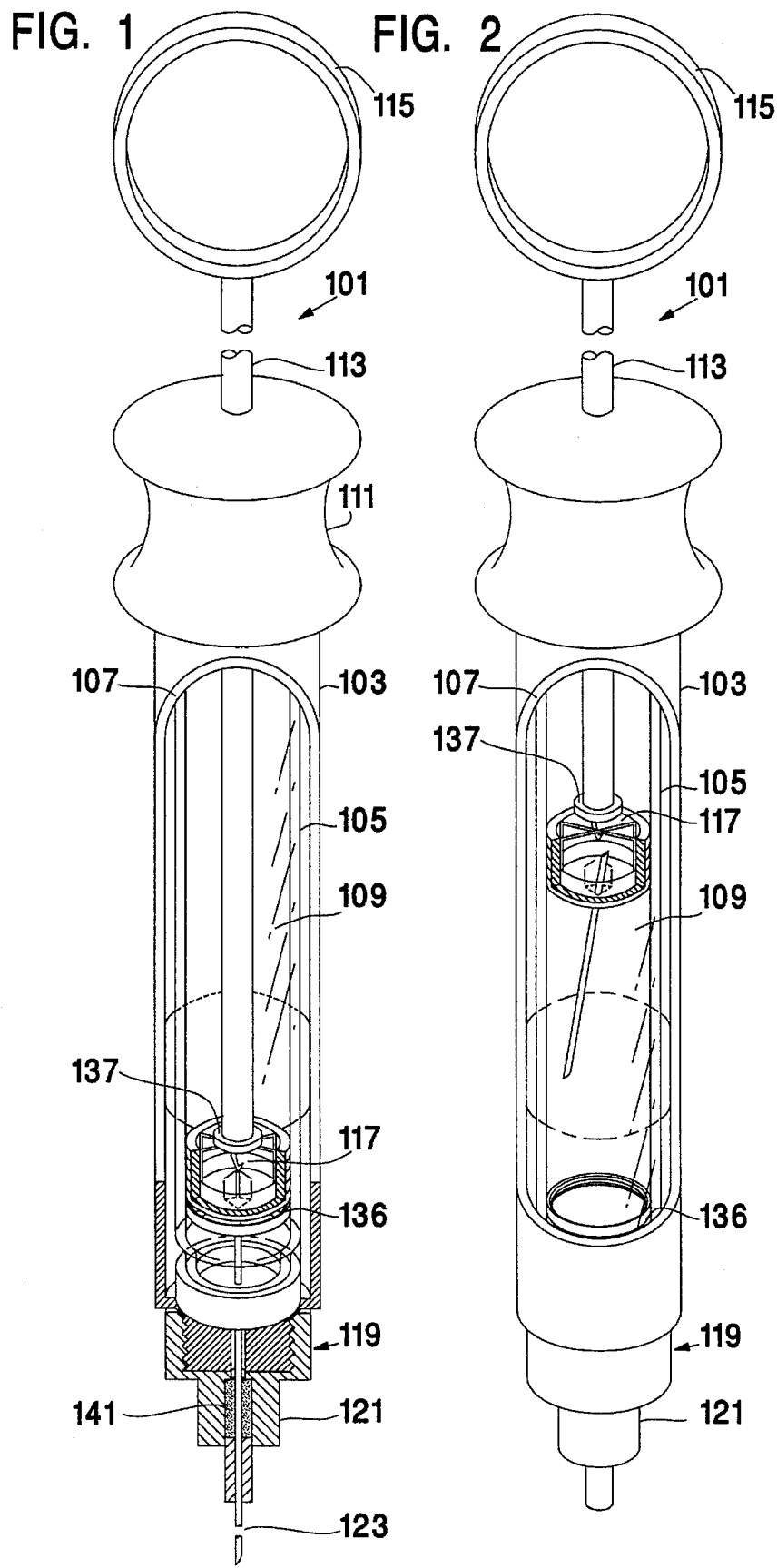

5,501,670

1

SYRINGE SYSTEM PROVIDING RETRACTION OF NEEDLE CANNULA INTO DISPOSABLE CARTRIDGE

BACKGROUND OF THE INVENTION

The present invention relates to hypodermic syringes used to inject medication into human or animal tissue. In particular, the invention pertains to cartridge-type syringes having a chamber that accepts a pre-filled disposable ampoule cartridge containing medicant to be injected.

A reusable hypodermic syringe employing a disposable medicant cartridge and needle assembly is the predominant system used by dentists for the delivery of local anesthetics, e.g., carbocaine and octocaine. Such syringes are used for other injection procedures as well. The conventional system presents the caregiver with the problem of handling the distal end of the syringe to detach, dismantle and properly dispose of the needle assembly following the injection procedure.

A conventional cartridge-based syringe 1 is illustrated in FIG. 8. One such device is the ASTRA 9002-00 dental syringe, available from Gainor Medical Supply of McDonough, Ga. Syringe 1 comprises a main body 3 of stainless steel providing an elongated cylindrical chamber 5 for receiving through a front side aperture 6 a medicant filled fluid cartridge 7. On the rear side of body 3 is a smaller aperture 8 sized to allow the user to push with his/her finger a spent cartridge 7 back out of chamber 5, through aperture 6. Cartridge 7 has an elongated tubular body which is typically made of glass. One end of cartridge 7 is closed-off by an axially slidable elastomeric piston 9 providing a fluid-tight seal. The opposite end of cartridge 7 is sealed by a cap 11 having a centrally located pierceable diaphragm.

Fixedly attached to main body 3 is a contoured, generally spool-shaped finger grip 13. Grip 13 has a hollowed-out interior portion 15. Grip 13 also has a smaller axially centered passageway for slidably receiving an elongated plunger stem 17. Attached to a proximal end of plunger stem 17 is a plunger ring 19 designed to accommodate a user's thumb. Together, ring 19 and grip 13 allow precise finger control over the axial movement and position of plunger stem 17. Attached to the distal end of plunger stem 17 is a barbed plunger hook 21. Within interior portion 15 resides a coil spring 16, and a spring cup 18 attached to stem 17. These components serve to provide a slight bias of plunger hook 21 against piston 9 when cartridge 7 is positioned within chamber 5.

Threadably received on the distal end of main body 3 is a disposable needle assembly 23 comprising a needle hub 25, and a needle cannula 27 fixedly secured within hub 25 by a tight pressure fit provided, e.g., by a metal crimp ring 28. The proximal end of needle cannula 27 is pointed and protrudes from hub 25. When hub 25 is threaded onto the distal end of main body 3, needle cannula 27 extends into the lower part of chamber 5.

To use syringe 1, cartridge 7 is inserted into chamber 5, and the distal end of needle cannula 27 is caused to penetrate tissue at the desired injection location. Next, plunger stem 17 is advanced whereby cartridge 7 is pushed toward the distal end of chamber 5 and into contact with the protruding proximal end of needle cannula 27. Through application of additional finger pressure, the protruding proximal end of needle cannula 27 is caused to pierce cap 11 and enter cartridge 7. This pressure also causes the distal end of hook 21 to become embedded in piston 9. Thereafter, piston 9 advances within cartridge 7 to expel the medicant through needle cannula 27 and into the tissue.

The needle disposal method is less than ideal with conventional syringe 1. Typically, the entire needle assembly 23 is detached from main body 3 and disposed of in a special container. Since the needle is wholly exposed, it is also a good practice to cut or break-off the nee, die tip. This procedure is cumbersome and not always practical while working on a patient. As a result, the used needle may not be immediately properly disposed of. This significantly increases the risk of accidental needle strikes. Moreover, needles disposed of in this manner present a potential hazard to those that must handle removal of medical waste.

The potential for accidental needle strikes to health care givers and associated personnel poses a significant health risk. Needle strikes cause painful wounds, and can result in local infections or, worse yet, transmission of communicable diseases such as hepatitis. The problem has become particularly acute with the increasing treatment and care of those infected with HIV. At a minimum, a needle strike victim is likely to experience a high degree of anxiety over the possibility of adverse health consequences, and expensive testing for communicable diseases may be necessary.

The health risks associated with the conventional type of syringe extend beyond the medical community. Improper handling of medical waste can extend the risk of accidental needle strikes to children or others who may happen upon the waste, or lead to misuse of contaminated needles obtained by drug addicts rummaging through trash containers.

A syringe with a simple and reliable mechanism for providing needle retraction into a disposable medicant cartridge would contribute greatly to the reduction of the aforementioned health risks, and the spread of communicable diseases such as AIDS.

In conventional syringes of the type illustrated in FIG. 6, the embedding of barbed hook 21 within piston 9 allows retraction of piston 9 during the injection procedure. This is useful, e.g., when injecting local anesthetic, in order to check for blood flow indicating an improper placement of the needle end within a blood vessel. This retraction feature does not allow for retraction of a used needle into the disposable cartridge, however. First, no mechanism is provided for securely attaching the used needle cannula to the piston for retraction. Secondly, needle cannula 27 is held very securely in the needle bore, e.g., by metal crimp ring 28, and any embedded attachment of hook 21 and needle cannula 27 to piston 9 is bound to be too weak to withstand the large pulling force required to break the bond of the needle within the needle bore.

Previous attempts to address the potential of retractable needles in cartridge-type syringe systems have been unduly complex and of uncertain reliability. None is designed to allow for ready conversion of a conventional syringe into a safety syringe providing needle retraction into a disposable cartridge.

Haber et al. U.S. Pat. No. 4,808,169 discloses a "Disposable Safety Syringe Having Means for Retracting Its Needle Cannula Into Its Medication Cartridge." To enable piston retraction, this device provides a pair of gripping arms on a distal plunger end that is adapted to grip a projecting plug member provided on a proximal side of a slidable cartridge piston. At the end of a distal piston stroke, the proximal end of the needle becomes embedded in the piston. Also, the cartridge distal end is forced into contact with a pair of rotatable needle retaining jaws provided on a distal end of the cartridge receiving barrel. This contact rotates the jaws out of engagement with the needle freeing the needle to be retracted, with the piston, into the disposable cartridge.

Operational difficulties are apparent in the Haber et al. system. The system depends for its proper operation on a firm connection between the piston and the needle during retraction, yet such a connection cannot be ensured by simply embedding the needle cannula in the piston material. Moreover, the system requires that a distally directed force be continually exerted by the cartridge against the needle gripping jaws, to maintain the needle freely movable in the distal bore during needle retraction. This could be difficult given that needle retraction requires a proximal retraction of the piston that would tend to pull the cartridge out of contact with the needle gripping jaws.

Schroeder U.S. Pat. No. 4,813,936 similarly discloses an arrangement for retracting a hypodermic needle into a disposable anesthetic carpule (cartridge). According to this patent, the retraction is accomplished by the provision of a pointed distal plunger end that becomes embedded in a proximal side of a slidable plug (piston) of the carpule, and by a barbed or threaded proximal end of the hypodermic needle that becomes embedded in a distal side of the slidable plug at the end of the injection stroke.

A projection on the needle prevents the needle from moving in the distal direction, but apparently the needle is free to move in the proximal direction. Hence, once the plunger distal end and the needle proximal end become embedded in the slidable plug, the needle can be retracted from the needle bore and into the carpule.

Operational difficulties are apparent in this system as well. First, since no positive mechanism is evident for preventing proximal movement of the needle in the needle bore, proximally directed pushing forces, such as may be generated when the pointed distal end of the needle is pressed into tissue, may cause inadvertent proximal displacement of the needle. On the other hand, the disclosed system, wherein the plunger distal end and the needle proximal end are imbedded into the movable carpule plug, does not assure that the needle can be reliably withdrawn in the event that additional means are provided for firmly holding the needle in the needle bore.

Accordingly, there is a need for a simple and reliable cartridge-type syringe that provides sure retraction of a needle cannula into a disposable medicant cartridge. Ideally, such a system would be readily adaptable for use with existing standard cartridge-type syringes, e.g., of the type illustrated in FIG. 8.

SUMMARY OF THE INVENTION

In view of the foregoing, it is a principal object of the present invention to provide a simple, reliable and cost effective cartridge-type syringe system that allows for sure and safe retraction of a needle cannula into a disposable medicant cartridge.

It is a further object of the invention to provide such a system that is readily adaptable for use with existing standard cartridge-type syringes, e.g., of the type illustrated in FIG. 8.

These and other objects are attained in accordance with a first aspect of the invention by a needle retracting piston for use in a disposable medicant cartridge for a syringe. The piston includes an elastomeric piston body axially slidable within a tubular cartridge body and a needle retraction unit mounted within the elastomeric piston body. The retraction unit includes a tensile strength member arranged for making engagement with a plunger hook to allow proximal retraction of the plunger body through the tubular cartridge body, and a needle receiving structure for interlocking, at the end of an injection stroke, with a proximal end of a needle cannula protruding into the cartridge body. This arrangement allows a used needle cannula to be retracted with the piston body into the cartridge.

In a second aspect of the invention, a needle retracting disposable medicant cartridge for a syringe includes a tubular cartridge body, a pierceable cap sealing off a distal end of the cartridge body, an elastomeric piston body axially slidable within the cartridge body, a fluid medicant contained within the cartridge body between the cap and piston body, and a needle retraction unit mounted within the elastomeric piston body. The needle retraction unit has a structure as mentioned above in connection with the first aspect of the invention.

In a third aspect of the invention, a disposable parts system is provided for use with a syringe of the type including a reusable syringe body providing a chamber for receiving a disposable medicant cartridge, and a plunger axially advanceable within the syringe body and having a plunger hook on a distal end thereof. The parts system includes a disposable medicant cartridge having a structure as described above in connection with the second aspect of the invention, and a needle/hub assembly. The needle/hub assembly includes a needle hub having mounting means for mounting the hub on a distal end of the reusable syringe body, a needle cannula positioned within the needle hub and protruding both distally and proximally therefrom, and bonding means for bonding the needle cannula within the needle hub and providing a break-away strength which is less than a needle retaining strength of the needle retraction unit. With this arrangement, in use, the needle cannula can be retracted with the piston body into the medicant cartridge.

These and other objects, features and advantages of the present invention will be evident and fully understood from the following detailed description of the preferred embodiments, taken in connection with the appended drawings.

BRIEF DESCRIPTION OF THE DRAWINGS

FIG. 1 is a front side perspective view of a fully assembled disposable cartridge-type syringe in accordance with the present invention, with a wedge-shaped section taken through a piston thereof and an axial section taken through a lower portion of the syringe body and needle hub. The position shown is the position assumed just after medicant has been substantially expelled from the disposable cartridge and just before needle engagement with the retraction mechanism begins.

FIG. 2 is a front side perspective view of the cartridge-type syringe shown in FIG. 1, with a wedge-shaped section taken through the piston, and showing a needle cannula engaged with the piston and retracted to a safe position within the disposable medicant cartridge.

DETAILED DESCRIPTION OF THE PREFERRED EMBODIMENTS

Figure 3:
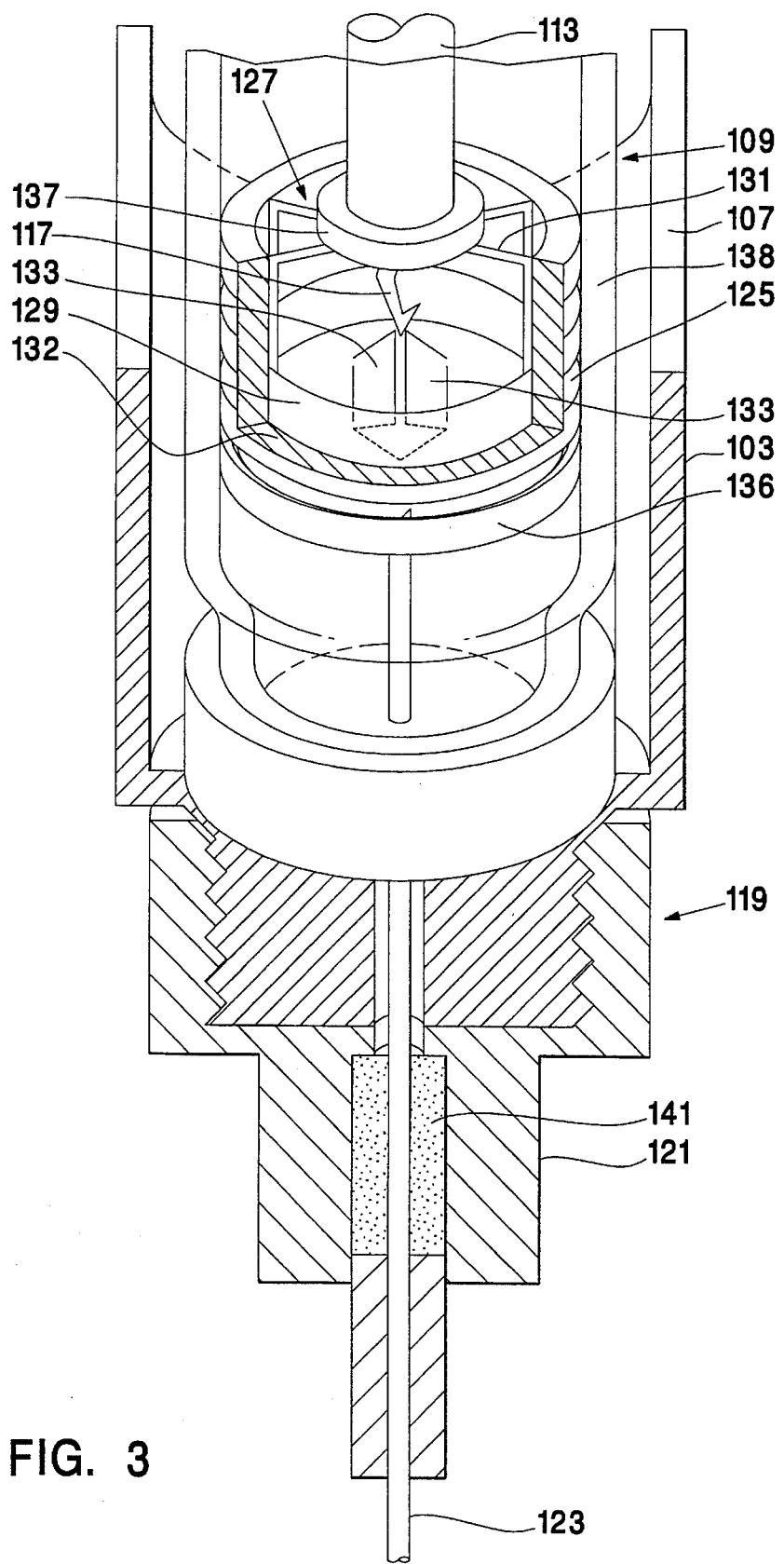
FIG. 3 is an enlarged fragmented perspective view of the lower portion of the syringe assembly shown in FIG. 1, with sections taken in the same manner as in FIG. 1.
Figure 8:
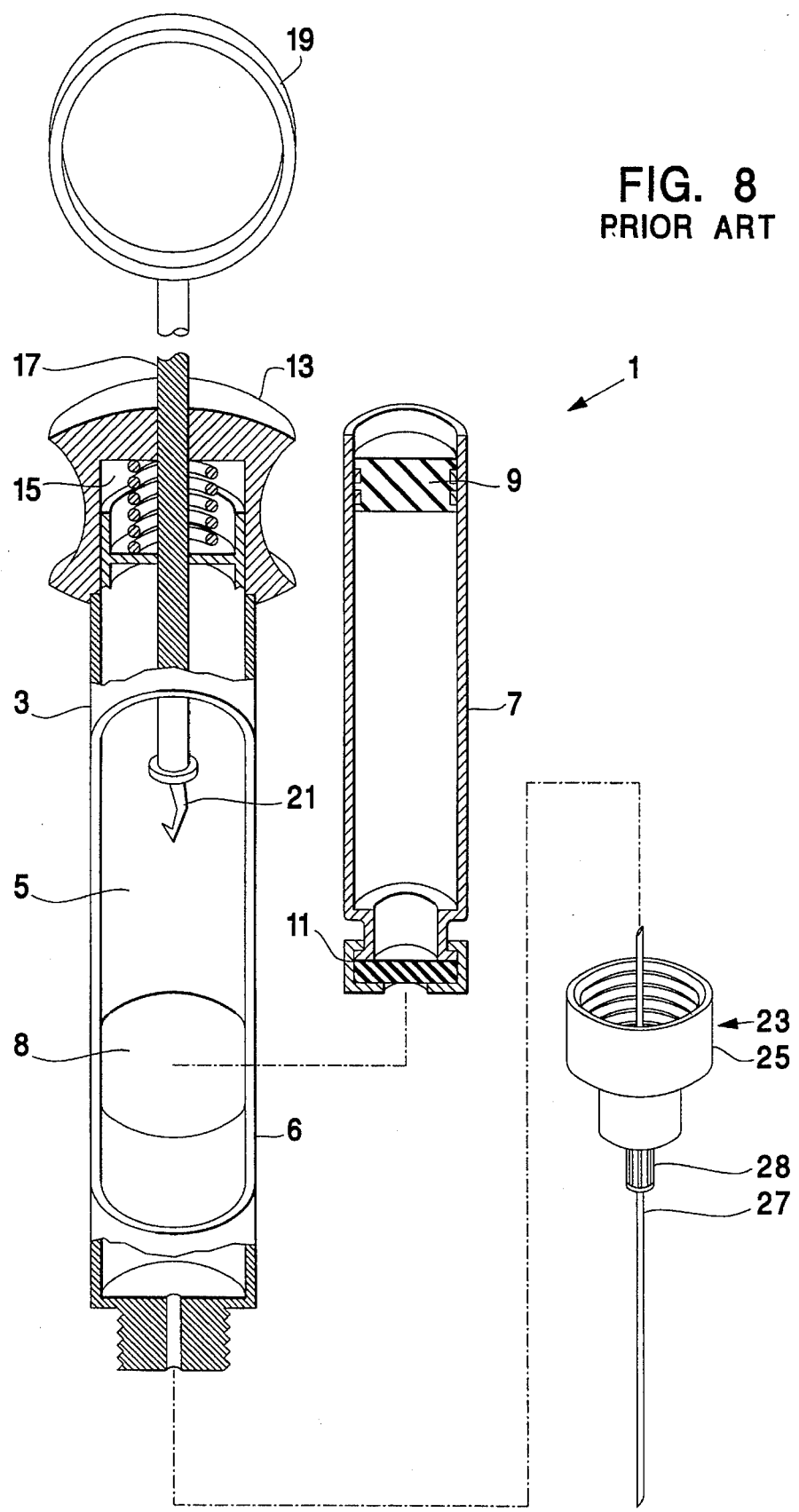
FIG. 8 is a partially exploded, partially sectioned, front side perspective view of a conventional (prior art) cartridge-type syringe system.

Referring first to FIGS. 1–3, a syringe 101 in accordance with the present invention has a structure corresponding in large part to the conventional syringe shown in FIG. 8. In fact, in the preferred embodiment, the only differences from the conventional arrangement are with respect to the disposable medicant cartridge, and the disposable needle assembly. In this manner, a conventional syringe can be readily converted into a safety syringe providing needle retraction into the disposable cartridge, simply by replacing the disposable parts. Since the structure of the conventional device has already been fully described hereinabove, the common structure of the present invention need only be described briefly. The focus here will be on the aforementioned different structure of the present invention.

As in the conventional arrangement, syringe 101 comprises a main body 103 providing an elongated cylindrical chamber 105 for receiving through a side aperture 107 a medicant filled fluid cartridge 109. Fluid cartridge 109 of the present invention is modified from the conventional cartridge design in order to provide for needle retraction into the cartridge, as will be described in detail hereinafter.

Fixedly attached to main body 103 is a spool-shaped finger grip 111. Although not visible, grip 111 has a hollowed-out interior portion housing a spring biasing mechanism as in the conventional syringe of FIG. 8. Grip 111 also has a smaller axially centered passageway for slidably receiving an elongated plunger stem 113. Attached to a proximal end of plunger stem 113 is a plunger ring 115 designed to accommodate a user's thumb. Together, ring 115 and grip 111 allow precise finger control over the axial movement and position of plunger stem 113. Attached to the distal end of plunger stem 113 is a barbed plunger hook 117.

Threadably received on the distal end of main body 103 is a disposable needle assembly 119 comprising a molded plastic needle hub 121, and a needle cannula 123 secured within hub 121. The proximal end of needle cannula 123 is pointed and protrudes from hub 121. When hub 121 is threaded onto the distal end of main body 103, needle cannula 123 extends into chamber 105. Needle assembly 119 of the present invention is modified from the conventional arrangement to allow needle cannula 123 to break-away from hub 121 in order to allow for needle retraction into cartridge 109, as will be described hereinafter.

Figure 4:
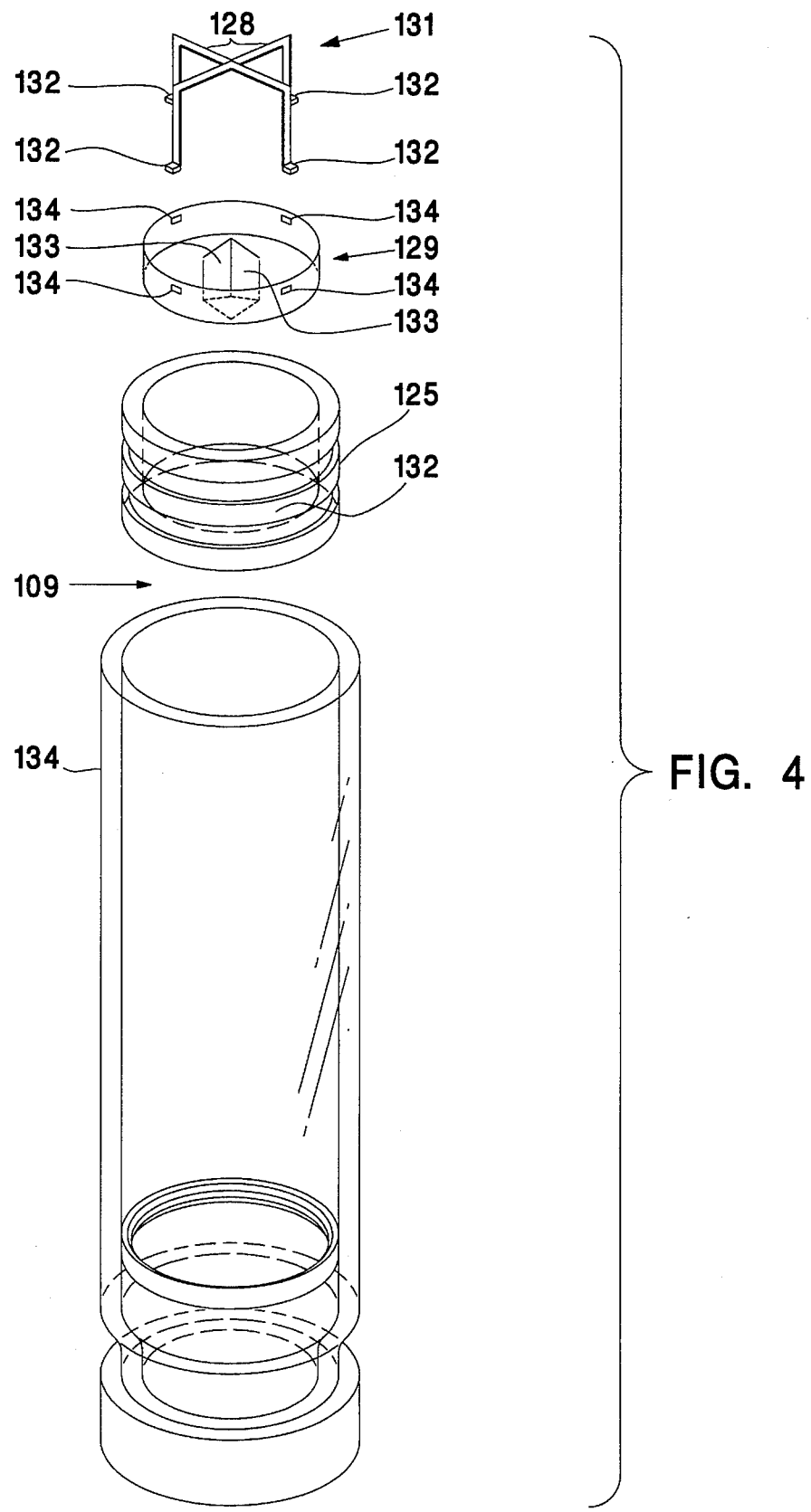
FIG. 4 is an exploded perspective view of the disposable medicant cartridge assembly received within the syringe of FIG. 1.
Figure 5:
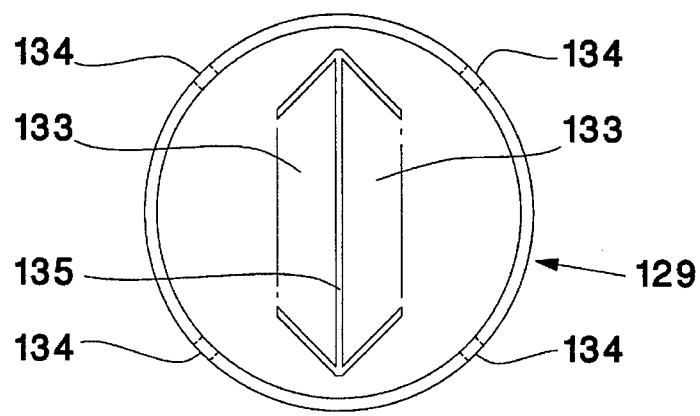
FIG. 5 is a top plan view of a needle receiving cup secured within the distal end of the piston of the cartridge assembly shown in FIG. 4.

As best seen in FIGS. 3–5, a first aspect of the present invention involves a modified design of the slidable piston of the disposable medicant cartridge 109. In accordance with the present invention, the conventional solid rubber piston is replaced with a piston body 125 having substantially the same outward configuration, but having a hollowed-out interior within which a needle retraction unit 127 is received. Retraction unit 127 comprises a relatively rigid needle receiving cup 129 shaped and sized to fit snugly and securely within the piston distal end, and an interlocking relatively rigid retraction cage 131 provided to allow plunger hook 117 to positively engage therewith. While the interior of the piston body 125 is substantially hollowed out, a floor portion 132 remains. Cup 129 is seated against floor portion 132.

As best seen in FIG. 4, retraction cage 131 comprises two U-shaped arms having transversely extending grasping portions 128 that cross each other, and distally extending portions terminating in four feet 132 which interlock with corresponding slots 134 in the cylindrical wall of needle receiving cup 129. Alternatively, retraction cage 131 could be joined to needle receiving cup 129 by tack welds. Although the configuration shown has arms which are squared at the top of the cage, a rounded or tapered arm shape could be used to facilitate engagement of plunger hook 117 therewith. Likewise, the number and extending directions of the arms could be varied for the same purpose. Also, although not shown in the drawings, a circumferential ring could be affixed about the top or sides of the arms to provide yet another engagement location for plunger hook 117. Cage 131 is preferably made of metal, but can be made of other materials providing a pull strength that exceeds the break-away strength of needle cannula 123 in needle hub 121. In this manner, cage 131 serves as a tensile strength member, providing tensile strength significantly greater than is obtained in the conventional arrangement by simply embedding hook 117 in the elastomeric plunger material.

As best seen in FIG. 5, a one-way needle locking passage is formed by tabs cut or stamped into a bottom surface plate of needle receiving cup 129. The illustrated double arrow effect is merely exemplary of the numerous configurations that could be used. Therein, two centrally located tabs 133 having a truncated triangular shape converge in a proximal direction and are separated by a radially directed slit 135 having a width dimension slightly less than the diameter of needle cannula 123. Locking tabs 133 form a wedge that allows passage of needle cannula 123 in the proximal direction, but prevents removal in the distal direction. During an injection stroke, piston body 125 is moved distally through the glass cylinder 138 of cartridge 109 to expel the medicant contained therein. Near the end of the injection stroke, the proximal end of needle cannula 123 pierces floor portion 132 of piston body 125 and enters needle receiving cup 129, locking needle cannula 123 in place. Once needle cannula 123 is locked in place in cup 129, piston 125 is simply retracted proximally through cartridge 109 causing needle cannula 123 to be disengaged from the bore of needle hub 121, allowing cannula 123 to be withdrawn into cartridge 109 for safe handling and disposal. Advantageously, locking tabs 133 tend to cant needle cannula 123 on retraction (as seen in FIG. 2), thereby preventing the needle cannula from being re-exposed.

To alert a user that the retraction mechanism is about to be engaged, a ridge or protrusion 136 (shown as a circumferential ring) can be formed on the inside of glass cylinder 138, at the distal end thereof. Protrusion 136 could be formed separately and attached to cylinder 138, or integrally formed with glass cylinder 138. Protrusion 136 serves to cause a distinct click and tactile feedback when piston body 125 passes thereby (and locking tabs 133 begin to engage needle cannula 123). This occurs just before the end of an injection stroke is reached, and allows a user to terminate the injection stroke before needle engagement. In this manner, a single needle cannula can be used to inject medicant from successive cartridges.

By changing the configuration of locking tabs 133, the strength and flexibility of the tabs can be altered to obtain optimum needle locking characteristics. In this respect, the various locking tab configurations disclosed in the applicant's U.S. Pat. No. 5,382,235 may be used. (That patent is hereby incorporated by reference in its entirety.)

Retraction of piston body 125 is accomplished by engaging plunger hook 117 with retraction cage 131, and then pulling back on plunger stem 113. Unlike a simple embedding of hook 117 within the elastomeric piston material, retraction cage 131 assures a sufficiently strong attachment to overcome the break-away strength of the bond between needle cannula 123 and hub 121.

Figure 6:
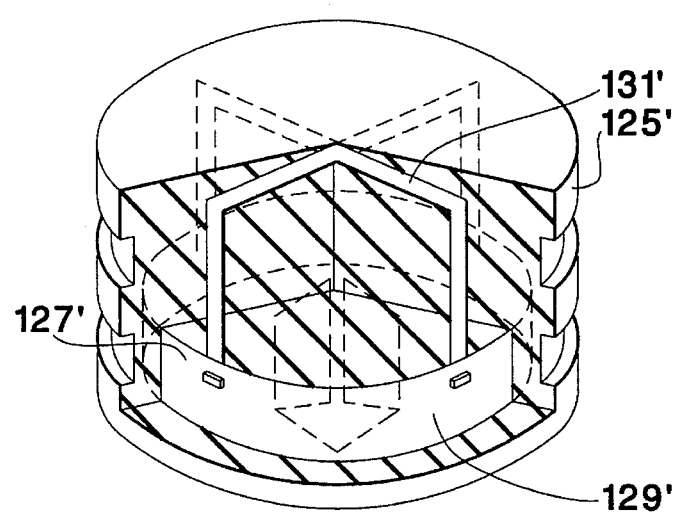
FIG. 6 is a perspective view of an alternative piston design embodying the principles of the invention, with a wedge-shaped section taken therethrough.

Piston body 125 can be molded with a hollow interior for accepting needle retraction unit 127, as illustrated in FIGS. 1–4. Alternatively, as shown in FIG. 6, a solid piston body 125' could be integrally molded with a needle retraction unit 127', whereby the retraction unit 127' would be encapsulated, partially or completely, by the elastomeric piston material. With the design of FIGS. 1–4, a circular flange 137 at the distal end of piston stem 113 pushes against the top of retraction cage 131 so that locking tabs 133 are protected from damage by contact with the plunger hook 117 during an injection stroke. With retraction unit 127' integrally molded with piston body 125', as shown in FIG. 6, the elastomeric piston material provides a pushing surface for contact with flange 137. So long as a relatively soft elastomeric material is used, encapsulation of cage 131' should not present a substantial impediment to rotation of hook 117, within the material, in order to make proper cage engagement. Another possibility would be to leave cage 131' substantially exposed and have only needle receiving cup 129' encapsulated by the elastomeric material. This would facilitate proper engagement of plunger hook 117 with cage 131, since nothing would inhibit rotation of hook 117 to obtain engagement with one of the cage arms.

Figure 7:
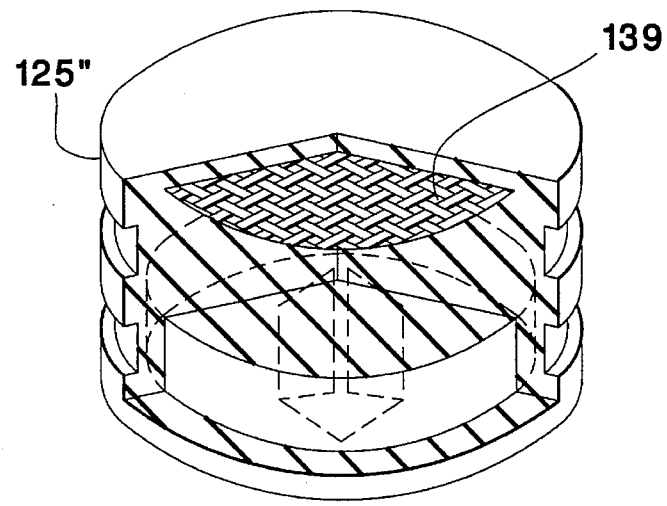
FIG. 7 is a second alternative piston design embodying the principles of the invention, with a wedge-shaped section taken therethrough.

Yet another possible piston configuration is illustrated in FIG. 7. In this embodiment, an embedded wire mesh or screen 139 is substituted for retraction cage 131'. With this arrangement, barbed hook 117 passes relatively freely through screen 139 and is embedded in plunger body 125'' during an injection stroke. When plunger stem 113 is pulled in the proximal direction, however, screen 139 ensnares hook 117 providing a strong tensile connection between plunger stem 113 and piston body 125'', whereby needle retraction can be effected in the manner previously described.

In accordance with the present invention, the conventional needle assembly is modified to assure that proper needle release is obtained for retraction thereof. To this end, needle cannula 123 is secured within needle hub 121 by a shrink-fit heat bond, or adhesive bond, retaining seal 141. Needle cannula 123 can be provided with grooves at the attachment location in order to strengthen the bond, if necessary. Alternatively, a metal crimp ring similar to the type used in the conventional arrangement of FIG. 8 could be used. In any case, the critical point is that the needle/hub bond should have a break-away strength that is less than the needle retaining strength of needle retraction unit 127. Tests have indicated the latter strength to be around 17 lbs. Preferably, the break-away strength of the needle/hub bond is in the range of 6–8 lbs. Within this range, sufficient strength to perform the injection procedure is assured, and at the same time substantial effort is not required to effect needle retraction. By way of comparison, in the conventional syringe arrangement, the break-away strength of the needle/hub bond is in the range of 30–40 lbs. Presently, FDA guidelines (ISO standards) specify minimum bond strengths between hypodermic needles/hubs in the range of 7.65 lbs–15.52 lbs, for needle gauges between 25 and 18. It is believed that approval for lesser bond strengths will be obtainable for applications/devices as described herein.

In a preferred embodiment, the needle/hub bond is created using Loctite™ #3001 adhesive. Tests have shown that with this adhesive the break-away strength can be accurately determined based upon the needle surface area coverage. In particular, this adhesive appears to provide an adherence of about 1 lb per 0.0008 –0.0010 square inch of needle surface area coverage.

When piston body 125 is moved proximally through cartridge 109 with needle cannula 123 locked in receiving cup 129, retaining seal 141 around needle cannula 123 is broken and the needle cannula can be retracted into cartridge 109 for safe and efficient disposal. The safe placement of needle cannula 123 can be effected immediately upon completion of an injection procedure, thus minimizing the possibility of accidental needle strikes.

Needle cannula 123 should have a side loading fluid port located sufficiently distally from the proximal end of needle cannula 123 so that it will not become blocked by engagement of the cannula with piston body 125. In this manner, it is possible to expel all of the medicant from the cartridge. A side loading port can also serve to strengthen the engagement of needle cannula 123 between locking tabs 133, and assist in canting the needle cannula as shown in FIG. 2 so that it cannot be re-exposed.

The present invention has been described in terms of preferred embodiments thereof. Numerous other embodiments, features and modifications within the spirit and scope of the invention will occur to those having ordinary skill in the art, upon reading this disclosure.

I claim:

1. A needle retracting piston for use in a disposable medicant cartridge for a syringe, comprising:

an elastomeric piston body axially slidable within a tubular cartridge body; and a needle retraction unit mounted within said elastomeric piston body, said unit including a tensile strength member arranged for making engagement with a plunger hook to allow proximal retraction of said plunger body through said tubular cartridge body, and a needle receiving structure for interlocking, at the end of an injection stroke, with a proximal end of a needle cannula protruding into said cartridge body, whereby a used needle cannula can be retracted with said piston body into said cartridge.

2. A needle retracting piston according to claim 1, wherein said tensile strength member comprises at least one arm, said arm having a grasping portion extending generally transversely with respect to said piston body, and at least one end portion attached to said needle receiving structure.

3. A needle retracting piston according to claim 1, wherein said needle receiving structure comprises a relatively rigid needle receiving plate having tabs formed therein, said tabs defining a wedge that allows passage of a needle cannula in a proximal direction and prevents removal of the needle cannula in a distal direction.

4. A needle retracting piston according to claim 3, wherein said needle receiving plate is formed as part of a needle receiving cup having upstanding walls.

5. A needle retracting piston according to claim 4, wherein said tensile strength member comprises a cage structure including a pair of arms, said arms each having a grasping portion extending generally transversely with respect to said piston body and crossing each other, and end portions attached to the upstanding walls of said needle receiving cup.

6. A needle retracting piston according to claim 1, wherein said needle retraction unit is integrally molded with said elastomeric piston body and at least partially encapsulated thereby.

7. A needle retracting piston according to claim 6, wherein said needle retraction unit is wholly encapsulated by said elastomeric piston body.

8. A needle retracting piston according to claim 1, wherein said elastomeric piston body has a hollow interior within which said needle retraction unit is received.

9. A needle retracting piston according to claim 1, wherein said tensile strength member comprises a wire mesh embedded within said elastomeric piston body, said wire mesh serving to ensnare a plunger hook that passes therethrough.

10. A needle retracting disposable medicant cartridge for a syringe, comprising:
   a tubular cartridge body;
   a pierceable cap sealing off a distal end of said cartridge body;
   an elastomeric piston body axially slidable within said cartridge body;
   a fluid medicant contained within said cartridge body between said cap and piston body; and
   a needle retraction unit mounted within said elastomeric piston body, said unit including a tensile strength member arranged for making engagement with a plunger hook to allow proximal retraction of said plunger body through said tubular cartridge body, and a needle receiving structure for interlocking, at the end of an injection stroke, with a proximal end of a needle cannula protruding into said cartridge body, whereby a used needle cannula can be retracted with said piston body into said cartridge.

11. A needle retracting disposable medicant cartridge according to claim 10, wherein said cartridge body includes on its inside surface, adjacent a distal end thereof, a protrusion for providing tactile feedback when the piston passes thereby, whereby a user is alerted that an end of an injection stroke is approaching and the needle retraction mechanism is about to be engaged.

12. A needle retracting disposable medicant cartridge according to claim 11, wherein said protrusion comprises a circumferential ring.

13. A disposable parts system for use with a syringe of the type including a reusable syringe body providing a chamber for receiving a disposable medicant cartridge, and a plunger axially advanceable within said syringe body and having a plunger hook on a distal end thereof, said parts system comprising:
   a disposable medicant cartridge, said cartridge including:
      a tubular cartridge body;
      a pierceable cap sealing off a distal end of said cartridge body;
      an elastomeric piston body axially slidable within said cartridge body;
      a fluid medicant contained within said cartridge body between said cap and piston body; and
      a needle retraction unit mounted within said elastomeric piston body, said unit including a tensile strength member arranged for making engagement with said plunger hook to allow proximal retraction of said plunger body through said tubular cartridge body, and a needle receiving structure for interlocking, at the end of an injection stroke, with a proximal end of a needle cannula protruding into said cartridge body; and
   a needle/hub assembly including:
      a needle hub having mounting means for mounting said hub on a distal end of said reusable syringe body;
      a needle cannula positioned within said needle hub and protruding both distally and proximally therefrom; and
      bonding means for bonding said needle cannula within said needle hub and providing a break-away strength which is less than a needle retaining strength of said needle retraction unit, whereby, in use, said needle cannula can be retracted with said piston body into said cartridge.

14. A disposable parts system according to claim 13, wherein said bonding means comprises an adhesive.

15. A disposable parts system according to claim 13, wherein said bonding means comprises a shrink-fit heat bond.

16. A disposable parts system according to claim 13, wherein said break-away strength is less than 17 lbs.

17. A disposable parts system according to claim 16, wherein said break-away strength is in the range of approximately six to eight lbs.

* * * * *